United States Patent
Wang et al.

[11] Patent Number: 5,869,507
[45] Date of Patent: Feb. 9, 1999

[54] AZATYROSINE ANALOGUES

[75] Inventors: Hui-Po Wang, No. 1, Sec. 1, Jan-ai Rd.; On Lee; Jin-Yuh Shew, all of Taipei; Shui-Jane Lee, Tainan Shuan, all of Taiwan

[73] Assignees: Hui-Po Wang; Hansen Tsai, both of Taipei, Taiwan

[21] Appl. No.: 899,859

[22] Filed: Jul. 24, 1997

[51] Int. Cl.[6] .......................... A61K 31/44; C07D 213/65
[52] U.S. Cl. ............................................ 514/351; 546/300
[58] Field of Search ............................... 546/300; 514/351

[56] References Cited

PUBLICATIONS

Cooper et al, "A concise synthesis of either, etc" CA 126:75208, 1996.

*Primary Examiner*—Patricia L. Morris

*Attorney, Agent, or Firm*—Bacon & Thomas

[57] ABSTRACT

A novel anti-oncogenic azatyrosine analogues of formula (I)

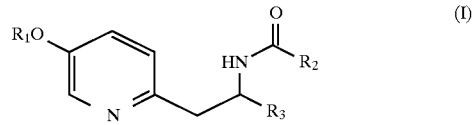

wherein $R_1$ is $C_{1-6}$ alkyl, $C_{1-6}$ haloalkyl, benzyl, or ($C_{1-6}$ alkyl)carbonyl; $R_2$ is $C_{1-6}$ alkyl, $C_{1-6}$ haloalkyl, or $C_{1-6}$ alkoxyl; and $R_3$ is $CONR_4R_5$, $CONHNR_4R_5$, or $COOR_6$, wherein each $R_4$ and $R_5$ independently is a hydrogen, $C_{1-6}$ alkyl, $C_{2-6}$ alkenyl, $C_{2-6}$ alkynyl, or $C_{3-6}$ cycloalkyl, or $R_4$ and $R_5$ taken together with the nitrogen attached thereto form a $C_{3-8}$ heterocyclic group; $R_6$ is $C_{1-6}$ alkyl, $C_{1-6}$ haloalkyl, $C_{2-6}$ alkenyl, $C_{2-6}$ alkynyl, $C_{3-6}$ cycloalkyl, or benzyl. Also disclosed is a method of preparing such a novel anti-oncogenic azatyrosine analogues, as well as a pharmaceutical composition containing a compound of formula (I).

7 Claims, No Drawings

AZATYROSINE ANALOGUES

BACKGROUND OF THE INVENTION

Azatyrosine (L-b-(5-hydroxy-2-pyridyl)alanine), an antibiotic from *Streptomyces chibanensis* (Inouye, S.; Shomura, T.; Tsuruoka, T.; Ogawa Y.; Watanabe, H.; Yoshida, J.; Niida, T. *Chem. Pharm. Bull.* 1975, 23, 2669.), was first reported to suppress the growth of NIH 3T3 cells transformed by c-Ha-ras, c-Ki-ras, N-ras, or c-raf oncogene while having essentially no effect on the wild type cells (Shindo-Okada, N.; Makabe, O.; Nagallara, H.; Nishimura, *S. Mol. Carcinogen* 1989, 2, 159.). Those azatyrosine-treated transformed cells that survived reverted to an apparently normal phenotype, the normal appearance and growth characteristics of the cells persisted for months after removal of the compound (Krzyzosiak, W. J.; Shindo-Okada, N.; Teshima, H.; Nakajima, K.; Nishimura, S. *Proc, Natl. Acad. Sci. U.S.A.* 1992, 89, 4879.), and some of the revertant clone demonstrated complete loss of tumorigenicity on nude mice. Studies also proved that this compound is involved in the regulation of other oncogenic cell growth (Chung, D. L.; Brandt-llauf, P.; Murphye, R. B.; Nishimura, S.; Yamaizumi, Z.; Weinst:ein, l. B.; Pincuf, M. R. *Anticancer Res.* 1991, 11, 1373. Kyprianou, N.; Taylor-Papadimitriou, *J. Oncogene* 1992, 7, 57. Fujita-Yoshigaki, J.; Yokoyama, S.; Shindo-Okada, N.; Nlshimura, S. *Oncogene* 1992, 7, 2019. Nomura, T.; Ryoyama, K.; Okada, G.; Matano, S.; Nakamura, S.; Kameyama, T. *Jpn. J. Cancer Res.* 1992, 83, 851. Campa, M. J.; Glickman, J. F.; Yamamoto, K.; Chang, K. J. *Proc, Natl. Acad. Sci. U.S.A.* 1992, 89, 7654. Benoit, R. M.; Eiseman, J.; Jacobs, S. C.; Kyprianou, N. *Urology* 1995, 46, 370.). In addition, L-azatyrosine inhibits 7,12-dimethylbenz[a]anthracene or methylnitrosourea-induced carcinogenesis in mice harboring a normal c-Ha-ras gene ( Izawa, M.; Takaysma, S.; Shindo-Okada, N.; Doi, S.; Kimura, M.; Katsuki, M.; Nishimura, S. *Cancer Res.* 1992, 52, 1628.). The high reversion efficiency toward oncogenic transformed cells combined with low toxicity to normal cells suggested azatyrosine to be a new lead for developing anticancer agents (Ye, B.; Otaka, A.; Jr. Bruke, T. R. *Synlett* 1996, 459. Copper, M. S.; Seton, A. W.; Stevens, M. F. G.; Westwell, A. D. *Bioorg. Med. Chem. Lett.* 1996, 6, 2613.).

Although azatyrosine exhibited selective toxicity against ras-transformed tumor cells, the potential of this compound in cancer treatment is limited due to its potency. Relatively high concentrations up to 1–2 mM are necessary for the actvity (Shindo-Okada, N.; Makabe, O.; Nagallara, H.; Nishimura, S. *Mol. Carcinogen* 1989, 2, 159. Fujita-Yoshigaki, J.; Yokoyama, S.; Shindo-Okada, N.; Nlshimura, S. *Oncogene* 1992, 7, 2019. Benoit, R. M.; Eiseman, J.; Jacobs, S. C.; Kyprianou, N. *Urology* 1995, 46, 370.). It is believed that low activity demonstrated by azatyrosine is partially due to its low intracellular bioavailability, which is probably due to its amphoteric structure in nature. The increase of intracellular bioavailability of this drug thus becomes important for improving its antitumor activity.

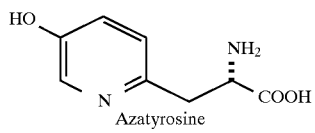
Azatyrosine

Reports indicated that azatyrosine was synthesized via a seven-step synthetic route shown in Scheme 1 (Norton, S. J. et al *J. Org. Chem.,* 1961, 26, 1495–8.) and a eight-step synthetic route shown in Scheme 2 (Makabe et al 2–273659 1989.). The Norton method used expensive kojic acid as starting material and multiple steps disclosed by Makabe et al lead to a low yield of azatyrosine.

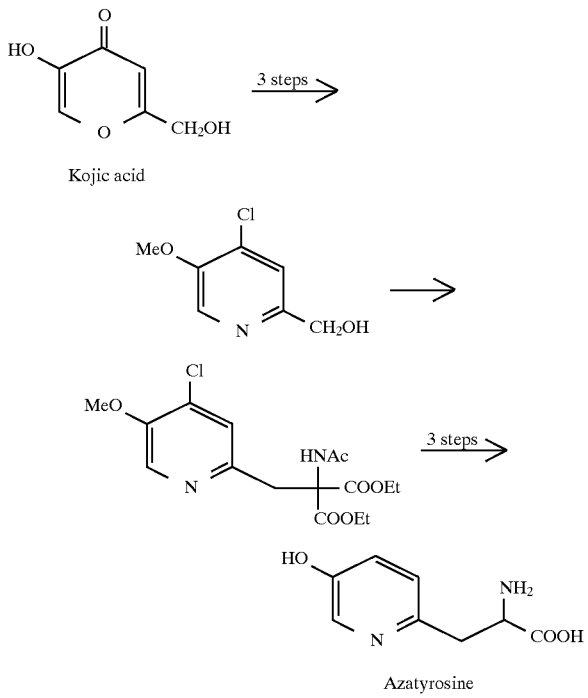

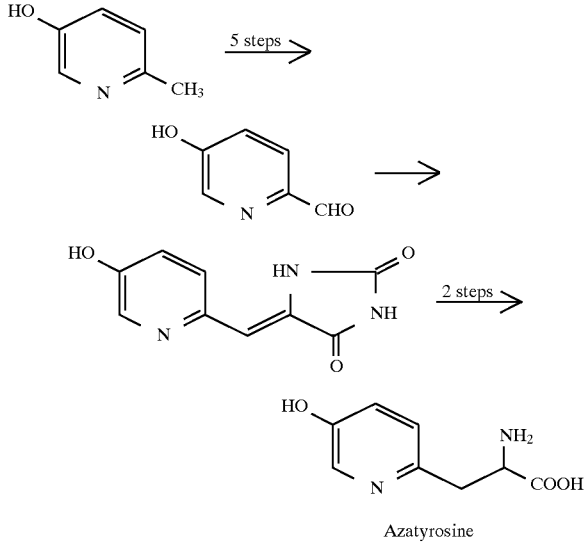

SUMMARY OF THE INVENTION

One aspect of this invention relates to novel azatyrosine analogues of formula (I)

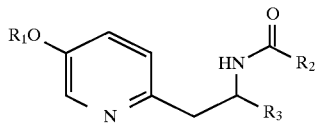

wherein R₁ is $C_{1-6}$ alkyl, $C_{1-6}$ haloalkyl, benzyl, or ($C_{1-6}$ alkyl)carbonyl, preferably benzyl;

R₂ is $C_{1-6}$ alkyl, $C_{1-6}$ haloalkyl, or $C_{1-6}$ alkoxyl, preferably i-butyloxy; and R₃ is CONR₄R₅, CONHNR₄R₅, or COOR₆, wherein each R₄ and R₅ independently is a hydrogen, $C_{1-6}$ alkyl, $C_{2-6}$ alkenyl, $C_{2-6}$ alkynyl, or $C_{3-6}$ cycloalkyl, or R₄ and R₅ taken together with the nitrogen attached thereto form a $C_{3-8}$ heterocyclic group, said heterocyclic group contains carbon atoms, at least one nitrogen atom and with or without futher heteroatom (e.g. N, O, S, or P); R₆ is $C_{1-6}$ alkyl, $C_{1-6}$ haloalkyl, $C_{2-6}$ alkenyl, $C_{2-6}$ alkynyl, $C_{3-6}$ cycloalkyl, or benzyl.

Another aspect of this invention relates to a pharmaceutical composition comprising a compound having the formula (I)

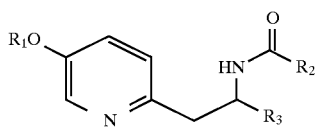

wherein R₁ is $C_{1-6}$ alkyl, $C_{1-6}$ haloalkyl, benzyl, or ($C_{1-6}$ alkyl)carbonyl;

R₂ is $C_{1-6}$ alkyl, $C_{1-6}$ haloalkyl, or $C_{1-6}$ alkoxyl; and

R₃ is CONR₄R₅, CONHNR₄R₅, or COOR₆, wherein each R₄ and R₅ independently is a hydrogen, $C_{1-6}$ alkyl, $C_{2-6}$ alkenyl, $C_{2-6}$ alkynyl, or $C_{3-6}$ cycloalkyl, or R₄ and R₅ taken together with the nitrogen attached thereto form a $C_{3-8}$ heterocyclic group; R₆ is $C_{1-6}$ alkyl, $C_{1-6}$ haloalkyl, $C_{2-6}$ alkenyl, $C_{2-6}$ alkynyl, $C_{3-6}$ cycloalkyl, or benzyl; and a pharmaceutically acceptable carrier.

Further aspect of this invention relates to a process for the preparation of formula (I), which comprises reacting a compound of formula (V)

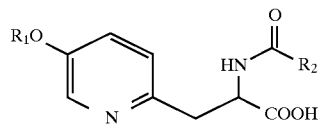

wherein R₁ and R₂ are defined the same as above, with HNR₄R₅, H₂NNR₄R₅, R₆X, or R₆OH, wherein R₄, R₅, and R₆ are defined the same as above, and X is halogen (e.g., F, Cl, Br, and I).

The inhibition of the compounds of formula (I) on ras-transformed NIH 3T3 cell lines, in comparison with the inhibition on wild type NIH 3T3 cell lines, are investigated in the present invention. Most of the compounds exhibited inhibitory effect on ras-transformed NIH 3T3 cells with activities higher than that of azatyrosine. Compound 12 for example had $IC_{50}$ 458 fold lower than that of azatyrosine. The compounds showed high inhibitory activity on ras-transformed NIH 3T3 cells but low toxicity on wild type NIH 3T3 cell lines, indicating the high degree of selective toxicity on tumor cells. Compound 12, for example, showed $IC_{50\ wild\ type}/IC_{50\ ras-transformed}=138$. Both antitumor activity and selective toxicity against tumor cells exhibited by compounds of formula (I) indicated their potential use for cancer treatment.

DETAILED DESCRIPTION OF THE INVENTION

We disclosed here a novel method using 5-hydroxy-2-hydroxymethylpyridine (1) (Golebiewski et al, Bull. Pol. Acad. Sci. Chem., 1990, 38, 17–27) as starting material. Condensation of 2 with 1 afforded a malonate derivative (3a), which upon hydrolysis with aqueous acid afforded intermediate 4a (R₁=benzyl). Acid treatment of 4a gave azatyrosine. Reaction of 4 with acids, relevant acid anhydride or acyl chloride gave intermediates (V), which are key intermediates for the preparation of a series of compounds with formula I (Scheme 3).

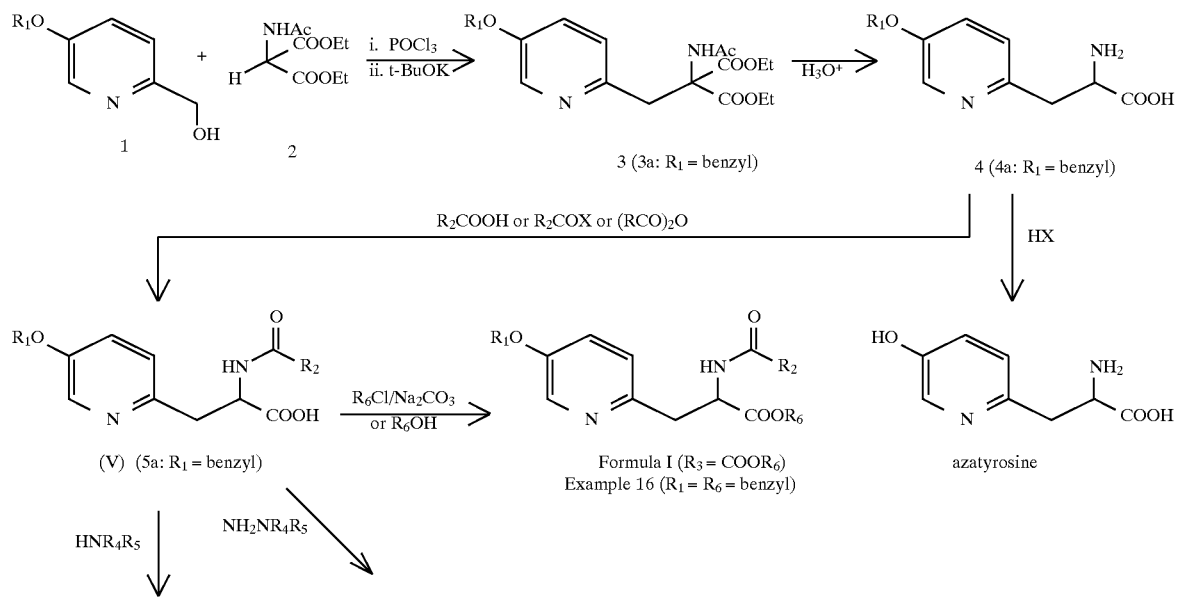

Scheme 3

-continued
Scheme 3

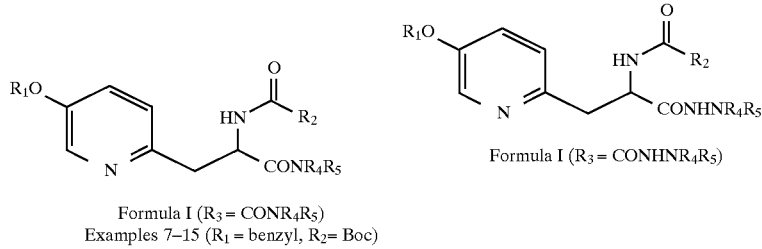

Formula I (R₃ = CONR₄R₅)
Examples 7–15 (R₁ = benzyl, R₂ = Boc)

Formula I (R₃ = CONHNR₄R₅)

The synthesized compounds were screened on wild type and ras-transformed NIH 3T3 cells for inhibitory activity. The inhibitory activity of compounds 7–15 is summarized in Table 1. As relative activity, defined as the ratio of $IC_{50}$ of azatyrosine to $IC_{50}$ of the test compound against ras-transformed NIH 3T3 cell line, was compared, most of the compounds exhibited higher activities than that of azatyrosine. Compound 12 for example showed $IC_{50}=16.5\pm2.2$ mM, a concentration 458 fold lower than that of azatyrosine. The compounds also exhibited selective toxicity on ras-transformed cells. The selectivity index (SI), defined as $IC_{50\ wild\ type}/IC_{50\ ras-transformed}$, of compound 12 was 138.5, indicating high selective toxicity on the tumorigenic ras-transformed cells.

solution containing diethyl 2-acetamido malonate (56.48 g, 0.26 mol) and potassium t-butoxide (30.30 g, 0.27 mol). The mixture was stirred at room temperature for 8 hours. Dimethylformamide was removed in vacuo and the residue was partitioned between dichloromethane and water. The dichloromethane solution was separated, dried over magnesium sulfate and concentrated in vacuo to dryness. The solid residue was chromatographed to give 97.4 g (94%) of compound 3 as white solid; mp 91°–92° C.; ¹H NMR (200 MHz, CDCl₃): d 8.182(1H, d, J=2.8 Hz, pyridine-α-H), 7.357(5H, m, Ph—H), 7.116(1H, d, J=2.8, 8.4 Hz, pyridine-γ-H), 6.953(1H, d, J=2.8, 8.4 Hz, pyridine-β-H), 6.771(1H, s, Ac—NH), 5.031(2H, S, Ph—CH₂—), 4.22(2H, q, J=7.0 Hz, COO—CH₂—), 3.731(2H, s, pyridine-CH₂—), 1.918

TABLE 1

Growth inhibition of azatyrosine and compounds of the following formula (I')
against wild type and ras-transformed NIH 3T3 cell lines.

(I')

|  |  |  | $IC_{50}$ (μM)[a] |  | Selective | Relative |
|---|---|---|---|---|---|---|
| Compounds | R₄ | R₅ | wild type | ras-transformed | toxicity[b] | activity[c] |
| azatyrosine | — |  | 10793.0 ± 471.8 | 7554.1 ± 417.5 | 1.4 | 1 |
| 7 | H | H | 1716.1 ± 10.4 | 73.1 ± 41.8 | 23.5 | 103 |
| 8 | n-propyl | H | 989.1 ± 707.3 | 34.1 ± 0.8 | 28.4 | 217 |
| 9 | allyl | H | 213.1 ± 111.5 | 74.1 ± 15.2 | 2.9 | 102 |
| 10 | propagyl | H | 410.1 ± 247.3 | 45.1 ± 1.65 | 9.0 | 165 |
| 11 | cyclopropyl | H | 1926.1 ± 898.7 | 104.5 ± 83.8 | 18.4 | 72 |
| 12 | cylcohexyl | H | 2284.1 ± 1763 | 16.1 ± 2.2 | 138.5 | 458 |
| 13 | —(CH₂)₅— |  | 74.8 ± 18.7 | 42.1 ± 3.9 | 1.8 | 180 |
| 14 | —(CH₂)₄— |  | 148.1 ± 12.5 | 59.1 ± 17.8 | 2.5 | 127 |
| 15 | —(CH₂)₂—S—(CH₂)₂— |  | 154.1 ± 3.9 | 50.1 ± 1.04 | 3.1 | 150 |

[a]Data are mean ± SD of 3–5 experiments.
[b]SI denotes IC₅₀ wild type/IC₅₀ ras-transformed cells.
[c]Ratio of the IC₅₀ of azatyrosine to the IC₅₀ of test compounds against ras-transformed NIH 3T3 cells.

Preparation 1.
Synthesis of diethyl 2-acetamido-2-((5-benzyloxypyridin-2-yl)methyl)malonate (Compound 3a)

A solution of 3-(5-benzyoxypyridin-2-yl)methanol (53.81 g, 0.25 mol) in dichloromethane (500 ml) was added dropwise to a solution of phosphoryl trichloride (38.33 g, 0.25 mol) in 1 L of dichloromethane. After stirring at room temperature for 24 hour the resultant solution was poured onto an aqueous Na₂CO₃ solution. The dichloromethane solution was separated, washed with brine and concentrated in vacuo. The crude product, 3-(5-benzyoxypyridin-2-yl) methyl chloride was then added to a dimethylformamide (3H, s, CH₃CO—), 1.246(3H, t, J=7.0 Hz, COO—CH₂—CH₃)ppm; IR (KBr) : 3400. 2975, 1750, 1725. 1675, 1575, 1490, 1475 cm⁻¹;EI Mass: 414, 341, 323, 295, 253; Elem. Anal.: Calc. C 63.76, H 6.32, N 6.76; Found C 63.72, H 6.33, N 6.69.

Preparation 2.
Synthesis of 3-(5-benzyoxypyridin-2-yl)-2-aminopropanoic Acid (Compound 4a)

A solution of diethyl 2-acetamido-2-((5-benzyloxypyridin-2-yl)methyl)malonate (Compound 3a, 41.45 g, 0.1 mol) in 500 ml of dilute hydrochloric acid was heated at reflux for 24 hours. The solution was diluted with 500 mL of water and neutralized with NaOH to pH 7.5–8.5. The precipitate was collected, washed with water and then with methanol to give 22.33 g (82%) of compound 4a ; mp 249°–252° C.;$^1$H NMR (80 MHz, D$_2$O+TFA): d 7.89(1H, s, pyridine-α-H), 7.54(2H, s, pyridine-a-H, pyridine-α), 7.54 (5H, m, Ph—H), 4.69(2H, S, Ph—CH$_2$—), 4.13(H, t, J=7.2 Hz, pyridine-CH$_2$—CH—), 3.24(H, d, J=7.2 Hz, pyridine-CH$_2$—)ppm; IR (KBr): 3436, 3035, 2964, 1620, 1590. 1573, 1504, 1500, 1416 cm$^{-1}$; Elem. Anal.: Calc. C 66.16, H 5.92, N 10.24; Found C 66.09, H 5.87, N 9.92.

Preparation 3.

Synthesis of 3-(5-hydroxypyridin-2-yl)-2-aminopropanoic Acid (Azatyrosine)

A mixture of 3-(5-benzyoxypyridin-2-yl)-2-aminopropanoic acid (Compound 4a, 13.62 g, 50 mmol) and 10% Pd/C (0.5 g) in water (500 ml) was subjected to hydrogenalysis under 1 atmosphere of hydrogen for 24 h. Pd/C was filtered off. The residue was condensed under reduced pressure. The solid residue was washed with methanol to give Azatyrosine (8.65 g, 95%): 248°–250° C. (decp.); Elem. Anal.: Calc. C 52.74 H 5.53 N 15.38, Found C 52.63 H 5.59 N 15.26.

Preparation 4.

Synthesis of 3-(5-benzyoxypyridin-2-yl)-2-t-butoxylcarbonylaminopropanoic Acid (Compound 5a)

A solution of (Boc)$_2$O (7.46 g, 35 mmol) in tetrahydrofuran (200 ml) was added to an 200 ml aqueous solution containing 3-(5-benzyoxypyridin-2-yl)-2-aminopropanoic acid (Compound 4a, 8.17 g, 30 mmol) and NaOH (1.32 g, 33 mmol) . The result solution was stirred at room temperature for 3 hours. tetrahydrofuran was evaporated in vacuo. The aqueous solution was acidified with potassium hydrogen sulfate to pH 3–4 and extracted with dichloromethane. The dichloromethane solution was separated, dried over magnesium sulfate and concentrated in vacuo to give 10.63 g (95%) of compound 5a; mp 156°–157.5° C.; $^1$H NMR (80 MHz, CDCl$_3$): d 9.16(1H, b, —COOH), 8.25(1H, d, pyridine-a-H) , 7.65–7.03(7H, m, pyridine-α-H, pyridine-α-H, Ph—H) , 5.70(1H, d, J=3.8 Hz, —NH) 5.08(2H, S, Ph—CH$_2$—), 4.42(1H, dt, J=5.06, 6.53 Hz, pyridine-CH$_2$—CH—), 3.29(2H, m, pyridine-CH$_2$—CH—), 1.43 (9H, s, t-Bu) ppm; IR (KBr): 3395, 2975, 1719, 1695. 1573, 1504 cm$^{-1}$; EI Mass: 372, 316, 277, 166, 91, 57; Elem. Anal.: Calc. C 64.50, H 6.50, N 7.52; Found C 63.67, H 6.82, N 7.02.

Preparation of compounds with Formula I—General Method

Alcohol, amine or hydrazine was added to a solution containing equimolar of compound 5 and coupling agents such as dicyclohexylcarbodiimide (DCC) or carbonyldiimidazole (CDI) in organic solvent such as dichloromethane or dimethylformamide. The solution was stirred at room temperature for 12 hour. The mixture was concentrated. The crude product was purified by recrystallization with appropriate solvents.

EXAMPLE 1

Synthesis of 3-(5-benzyoxypyridin-2-yl)-2-t-butoxylcarbonylamino NH$_3$ (Compound 7)

This compound was obtained by condensation of propylamine with compound 5a following General Method: mp 139°–139.5° C.; $^1$H NMR (80 MHz, CDCl$_3$): d 8.24(1H, d, J=1.74 Hz, pyridine-α-H), 7.37–7.18(7H, m, pyridine-α-H, pyridine-a-H, Ph—H), 6.16(1H, d, J=6.4 Hz, BocNH) 5.38 (2H, s, Ph—CH$_2$—), 4.50(1H, dd, J=6.14, 6.40 Hz, pyridine-CH$_2$—CH—), 3.17(2H, m, J=6.14 Hz, pyridine-CH$_2$—CH—), 2.30(2H, broad, —CONH$_2$), 1.40(9H, s, t-Bu) ppm; EI Mass: 371, 327, 271, 227, 199, 108, 91, 57; Elem. Anal.: Calc. C 64.67, H 6.78, N 11.31; Found C 64.71, H 6.58, N 11.37.

EXAMPLE 2

Synthesis of propyl 3-(5-benzyoxypyridin-2-yl)-2-t-butoxylcarbonylamino propanamide (Compound 8)

This compound was obtained by condensation of propylamine with compound 5a following General Method: mp 117°–117.5° C.; $^1$H NMR (200 MHz, CDCl$_3$): d 8.234(1H, d, J=2.6 Hz, pyridine-α-H), 7.37(5H, m, Ph—H), 7.169(1H, dd, J=2.6, 8.6 Hz, pyridine-α-H), 7.097(1H, d, J=8.6 Hz, pyridine-γ-H), 6.734(1H, broad, BocNH), 6.194(1H, d J=6.8 Hz, —CONH), 5.058(2H, s, Ph—CH$_2$—), 4.460(1H, broad, pyridine-CH$_2$—CH—), 3.113(4H, m, J=6.14 Hz, pyridine-CH$_2$—CHCONH—CH$_2$—), 1.407(9H, s, t-Bu), 1.357(2H, J=7.2 Hz, CONH—CH$_2$—CH$_2$—), 0.768(2H, t, J=7.2 Hz, CONH—CH$_2$—CH$_2$—CH$_3$)ppm; IR (KBr): 3323, 3258, 2972, 1697, 1646 cm$^{-1}$; EI Mass: 339, 248, 225, 91; Elem. Anal.: Calc. C 66.81, H 7.56, N 10.16; Found C 66.43, H 7.26, N 10.20.

EXAMPLE 3

Synthesis of N-cyclohexyl 3-(5-benzyoxypyridin-2-yl)-2-t-butoxylcarbonylaminopropanamide (Compound 12)

This compound was obtained by condensation of cyclohexylamine with compound 5a following General Method: mp 136°–136.5° C.; $^1$H NMR (200 MHz, CDCl$_3$): d 8.239 (1H, d, J=2.4 Hz, pyridine-α-H), 7.372(5H, m, Ph—H), 7.158(1H, dd, J=2.4, 8.4 Hz, pyridine-α-H), 7.088(1H, d, J=8.4 Hz, pyridine-γ-H), 6.585(1H, broad, BocNH), 6.164 (1H, d J=6.0 Hz, —CONH), 5.063(2H, s, Ph—CH$_2$—), 4.418(1H, broad, pyridine-CH$_2$—CH—), 3.653(1H, m, CONH—CH—), 3.175(1H, dd, J=6.0, 14.4 Hz, pyridine-CH$_2$—), 3.047(1H, dd, J=6.0, 14.4 Hz, pyridine-CH$_2$—), 1.405(9H, s, t-Bu), 1.720–0.750(10H, m, c-Hexyl)ppm; IR (KBr): 3348, 3313, 2931, 2851, 1651 cm$^{-1}$; EI Mass: 379, 288, 225, 91; Elem. Anal.: Calc. C 68.58, H 7.78, N 9.26; Found C 68.53, H 7.50, N 9.46.

EXAMPLE 4

Synthesis of benzyl 3-(5-benzyloxypyridin-2-yl)-2-aminopropionate (Compound 16)

A mixture of compound 4a, NaOH (1.188 g, 30 mmol) and (Boc)$_2$O (7.07 g, 32 mmol) in H$_2$O/THF was stirred at room temperature for 3 h. THF was evaporated. NaHCO$_3$ (1.36 g, 16 mmol) and a solution of benzyl chloride (5.08 g, 30 mmol) in CH$_2$Cl$_2$ was added. The mixture was stirred overnight. The CH$_2$Cl$_2$ layer was separated and subjected to trifluoroacetic acid (15.39 g, 135 mmol) treatment for 24 h. The solvent was evaporated. The residue was purified by chromatography to give compound 16 (46%); mp 143°–145° C.; $^1$H NMR (80 MHz, CDCl$_3$): d 8.08(1H, d, J=2.24 Hz, pyridine-α-H), 8.08(1H, dd, J=2.24, 8.96 Hz, pyridine-γ-H), 7.78(1H, d, J=8.96 Hz, pyridine-α-H), 7.41 (10H, m, Ph—H), 5.21(4H, m, Ph—CH$_2$—), 4.76(1H, t, J=7.60 Hz, pyridine-CH$_2$—CH—), 3.80(2H, d, J=7.60 Hz, pyridine-CH$_2$—CH—)ppm; IR (KBr): 3408, 3076, 2947, 1762, 1672. 1569, 1455 cm$^{-1}$; EI Mass: 227, 199, 136, 108, 91, 65.

Inhibition on the Growth of wild type and ras-transformed NIH 3T3 cells

The compounds of formula (I) were screened on wild type and ras-transformed NIH 3T3 cells for inhibitory activity. Screening was carried out in 96-well plate and the cells, with a density of 1500–2500 cells/well, were cultured in Dulbecco's modified Eagle's medium containing 10% fetal bovine serum at 37° C. under an atmosphere of 7.5% CO$_2$ in air. Growth curve for each cell line was established. The DMSO solution of each compound was incubated with the cell for 48 hours. Procedure of Hansen's MTT assay method was modified for estimating the cell number (Hansen, B. M., Nielson, S. E., Berg, K. *J. Immunol. Methods* 1989, 119, 203.). The absorption of generated formazan's blue at $l_{570\,nm}$ was recorded with ELISA reader. The number of surviving cells was determined from a calibration curve derived by correlating the absorption to the cell number determined from a hemacytometer. At least three experiments were carried out for each compound and $IC_{50}$ was calculated using sigmoidal regression (Parellada, J., Guinea, M. *J. Nat. Prod.*, 1995, 58, 823.). SI, the selectivity of growth inhibition of each test compound, was defined as the ratio of $IC_{50}$ against wild type to $IC_{50}$ against ras-transformed cell lines.

What is claimed is:

1. A compound of formula (I)

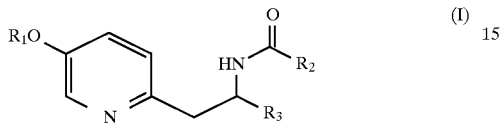

wherein $R_1$ is $C_{1-6}$ alkyl, $C_{1-6}$ haloalkyl, benzyl, or ($C_{1-6}$ alkyl)carbonyl;

$R_2$ is $C_{1-6}$ alkyl, $C_{1-6}$ haloalkyl, or $C_{1-6}$ alkoxyl; and $R_3$ is $CONR_4R_5$, $CONHNR_4R_5$, or $COOR_6$, wherein each $R_4$ and $R_5$ independently is a hydrogen, $C_{1-6}$ alkyl, $C_{2-6}$ alkenyl, $C_{2-6}$ alkynyl, or $C_{3-6}$ cycloalkyl;

$R_6$ is $C_{1-6}$ alkyl, $C_{1-6}$ haloalkyl, $C_{2-6}$ alkenyl, $C_{2-6}$ alkynyl, $C_{3-6}$ cycloalkyl, or benzyl.

2. A compound of claim 1, wherein $R_1$ is $C_{1-6}$ alkyl, or benzyl; $R_2$ is $C_{1-6}$ alkoxyl; and $R_3$ is $CONR_4R_5$ wherein each $R_4$ and $R_5$ independently is a hydrogen, $C_{1-6}$ alkyl, $C_{2-6}$ alkenyl, $C_{2-6}$ alkynyl, or $C_{3-6}$ cycloalkyl.

3. A compound of claim 1, wherein $R_1$ is $C_{1-6}$ alkyl, or benzyl; $R_2$ is $C_{1-6}$ alkoxyl; and $R_3$ is $COOR_6$, wherein $R_6$ is $C_{1-6}$ alkyl, $C_{1-6}$ haloalkyl, $C_{2-6}$ alkenyl, $C_{2-6}$ alkynyl, $C_{3-6}$ cycloalkyl, or benzyl.

4. A compound of claim 1, wherein $R_1$ is benzyl; $R_2$ is i-butyloxy; and $R_3$ is $CONR_4R_5$, wherein each $R_4$ and $R_5$ independently is a hydrogen, $C_{1-6}$ alkyl, $C_{2-6}$ alkenyl, $C_{2-6}$ alkynyl, or $C_{3-6}$ cycloalkyl.

5. A compound of claim 1, wherein $R_1$ is benzyl; $R_2$ is i-butyoxyl; and $R_3$ is $COOR_6$, wherein $R_6$ is $C_{1-6}$ alkyl, $C_{1-6}$ haloalkyl, $C_{2-6}$ alkenyl, $C_{2-6}$ alkynyl, $C_{3-6}$ cycloalkyl, or benzyl.

6. A compound of claim 4, wherein $R_4$ is hydrogen, $C_{1-6}$ alkyl, or $C_{3-6}$ cycloalkyl; $R_5$ is hydrogen.

7. A pharmaceutical composition comprising a compound having the formula (I)

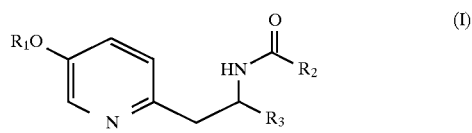

wherein $R_1$ is $C_{1-6}$ alkyl, $C_{1-6}$ haloalkyl, benzyl, or ($C_{1-6}$ alkyl)carbonyl;

$R_2$ is $C_{1-6}$ alkyl, $C_{1-6}$ haloalkyl, or $C_{1-6}$ alkoxyl; and $R_3$ is $CONR_4R_5$, $CONHNR_4R_5$, or $COOR_6$, wherein each $R_4$ and $R_5$ independently is a hydrogen, $C_{1-6}$ alkyl, $C_{2-6}$ alkenyl, $C_{2-6}$; alkenyl, or $C_{3-6}$ cyclonalkyl;

$R_6$ is $C_{1-6}$ alkyl, $C_{1-6}$ haloalkyl, $C_{2-6}$ alkenyl, $C_{2-6}$ alkynyl, $C_{3-6}$ cycloalkyl, or benzyl; and a pharmaceutically acceptable carrier.

* * * * *